(12) United States Patent
Rom

(10) Patent No.: US 8,335,564 B2
(45) Date of Patent: Dec. 18, 2012

(54) VENTRICLE PACING DURING ATRIAL FIBRILLATION EPISODES

(76) Inventor: Rami Rom, Or Akiva (IL)

(*) Notice: Subject to any disclaimer, the term of this patent is extended or adjusted under 35 U.S.C. 154(b) by 534 days.

(21) Appl. No.: 12/601,822

(22) PCT Filed: May 15, 2006

(86) PCT No.: PCT/IL2006/000571
§ 371 (c)(1),
(2), (4) Date: Nov. 25, 2009

(87) PCT Pub. No.: WO2006/126185
PCT Pub. Date: Nov. 30, 2006

(65) Prior Publication Data
US 2010/0185250 A1    Jul. 22, 2010

(51) Int. Cl.
*A61N 1/00* (2006.01)

(52) U.S. Cl. .......................................... 607/18

(58) Field of Classification Search ................ 607/5
See application file for complete search history.

(56) References Cited

U.S. PATENT DOCUMENTS

| | | | |
|---|---|---|---|
| 5,251,626 A * | 10/1993 | Nickolls et al. | 607/14 |
| 5,800,467 A * | 9/1998 | Park et al. | 607/17 |
| 6,242,988 B1 * | 6/2001 | Sarpeshkar | 331/111 |
| 7,280,989 B1 * | 10/2007 | Hoppensteadt et al. | 706/30 |
| 2003/0158587 A1 * | 8/2003 | Esteller et al. | 607/45 |

* cited by examiner

*Primary Examiner* — Niketa Patel
*Assistant Examiner* — Nadia Ahmad

(57) ABSTRACT

An adaptive cardiac resynchronization therapy system delivers biventricular stimulation to the heart with dynamic AV delay and VV interval. The stimulation is modified continuously in correlation with the hemodynamic performance of the heart. The system uses a spiking neural network comprising spike controller (42) that learns to associate the VA interval based on hemodynamic sensor temporal patterns. The associated VA interval replaces the sensed atrial event signal during atrial fibrillation episodes.

7 Claims, 4 Drawing Sheets

VENTRICLE PACING DURING ATRIAL FIBRILLATION EPISODES

FIELD OF THE INVENTION

The present invention relates generally to cardiac pacing and defibrillating and more specifically to cardiac pacing during arrhythmias.

BACKGROUND OF THE INVENTION

Atrial fibrillation (AF) is the most common cardiac rhythm disorder and it affects an estimated 2.3 million adults in the United States, the majority of who are over the age of 65 years. Far from benign, AF can lead to stroke, tachycardia-induced cardiomyopathy, and congestive heart failure. AF accounts for about 15% of all is strokes that occur each year in the United States. The number of patients with AF is increasing throughout the industrialized world as the population ages. In the United States, the prevalence of AF is expected to grow 2.5-fold to 5.6 million by 2050, and over half of those afflicted will be aged 80 or older As the burden of this disorder grows, increased emphasis will be placed on developing more effective ways to treat AF to reduce its associated morbidity and mortality (James L. Cox, MD, Surgical Management of Atrial Fibrillation, Medscape Cardiology, May 2005). Implanted pacemakers and intracardiac cardioverter defibrillators (ICD) deliver therapy to patients suffering from various heart-diseases (Clinical Cardiac Pacing and Defibrillation, $2^{nd}$ edition, Ellenbogen, Kay, Wilkoff, 2000). Dual chamber pacemakers pace the right ventricle with synchrony to the sensed atrial event, with a given delay, the atrioventricular (AV) delay. Cardiac Resynchronization Therapy (CRT) devices, i.e. biventricular pacemakers, pace both ventricles, and also synchronize according to the sensed atrial event signal.

However, a significant proportion of patients having a dual chamber pacemaker or biventricular pacemaker suffer also from atrial fibrillation episodes, possibly long lasting. These patients will not benefit from their dual chamber pacemaker or biventricular pacemaker during an episode since both devices synchronize according to the sensed atrial events that are not reliable during atrial fibrillation episodes, and hence will not deliver physiologic pacing during atrial fibrillation episodes.

In PCT publication WO0038782 a pacing system is disclosed, featuring a mode switching feature and ventricular rate regularization (VRR) function capable of stabilizing or regularizing ventricular heart rate during chronic or paroxysmal atrial tachyarrhythmia. The VRR function accomplishes this result by adjusting pacing rate according to the pattern of the most recent series of sensed or paced ventricular events.

In US2005187585 patent application, a method is disclosed for adaptively smoothing ventricular rate during atrial fibrillation (AF). According to this method, the pacing delivered by a pacing device is switched to a non-atrial synchronized mode when AF is detected. The ventricular escape interval (VEI) is modulated beat-by-beat around a physiological interval zone (PIZ), which is determined by the pre-arrhythmia ventricular rate or the output of rate responsive sensor.

Selective atrioventricular nodal (AVN) vagal stimulation (AVN-VS) has emerged as a novel strategy for ventricular rate (VR) control in atrial fibrillation (AF). AVN-VS is delivered to the epicardial fat pad that projects the parasympathetic nerve fibers to the AVN. Although AVN-VS preserves the physiological ventricular activation sequence, the resulting rate is slow and irregular. This issue is discussed in "Ventricular Rate Control by Selective Vagal Stimulation Is Superior to Rhythm Regularization by Atrioventricular Nodal Ablation and Pacing During Atrial Fibrillation", by Shaowei Zhuang, et al, Circulation. 2002; 106:1853. The authors indicate that the AVN-VS although producing a superior hemodynamic performance as compared to an ablation and pacing approach, results in irregular ventricular contractions rate, i.e. irregular sensed R-R intervals.

P. Taggart and P. Sutton argue In "Termination of Arrhythmia by Hemodynamic Unloading", published in Cardiac Mechano-Electric Feedback & Arrhythmia, by Kohl, Sachs and Franz, Elsevier Saunders, 2005, that hemodynamic unloading should be anti arrhythmic: "ventricular or atrial unloading should tend to be protective against focal tachycardia caused by triggered activity. The foregoing theoretical predictions are supported by several studies in different animal models in which arrhythmia were induced by increased stretch or volume loading."

The various methods presented above for rate regulation during atrial fibrillation episodes are based on heart rate regulation and do not take into account the exact cardiac cycle timings when pacing the ventricles during atrial fibrillation while the AVN-VS method preserves the physiological ventricular activation sequence but produces irregular ventricular contractions.

DETAILED DESCRIPTION OF THE PRESENT INVENTION

In the present invention implanted hemodynamic sensors are used in a way that reflects the hemodynamic performance of the ventricle, which is likely to be reliable also during atrial fibrillation episodes in order to unload hemodynamic stress and suppress the arrhythmia. The hemodynamic sensor can be used to synchronize pacing with the cardiac cycle timings and ventricular pacing in dual chamber devices or bi-ventricular pacing in CRT devices can be delivered with optimal timings also during atrial fibrillation episodes.

In accordance with the present invention, the timing of the subsequent atrial event is predicted relative to the preceding ventricle event by association of temporal patterns of hemodynamic sensor with a VA interval. By exploiting both this prediction and hemodynamic sensors that reflect ventricle function, a dynamic optimization of the pacing intervals can be performed for the particular patient. Such a combined tool is useful during atrial fibrillation incidents, and hence provides a more physiologic pacing for patients suffering from atrial fibrillation episodes.

Figure 1:
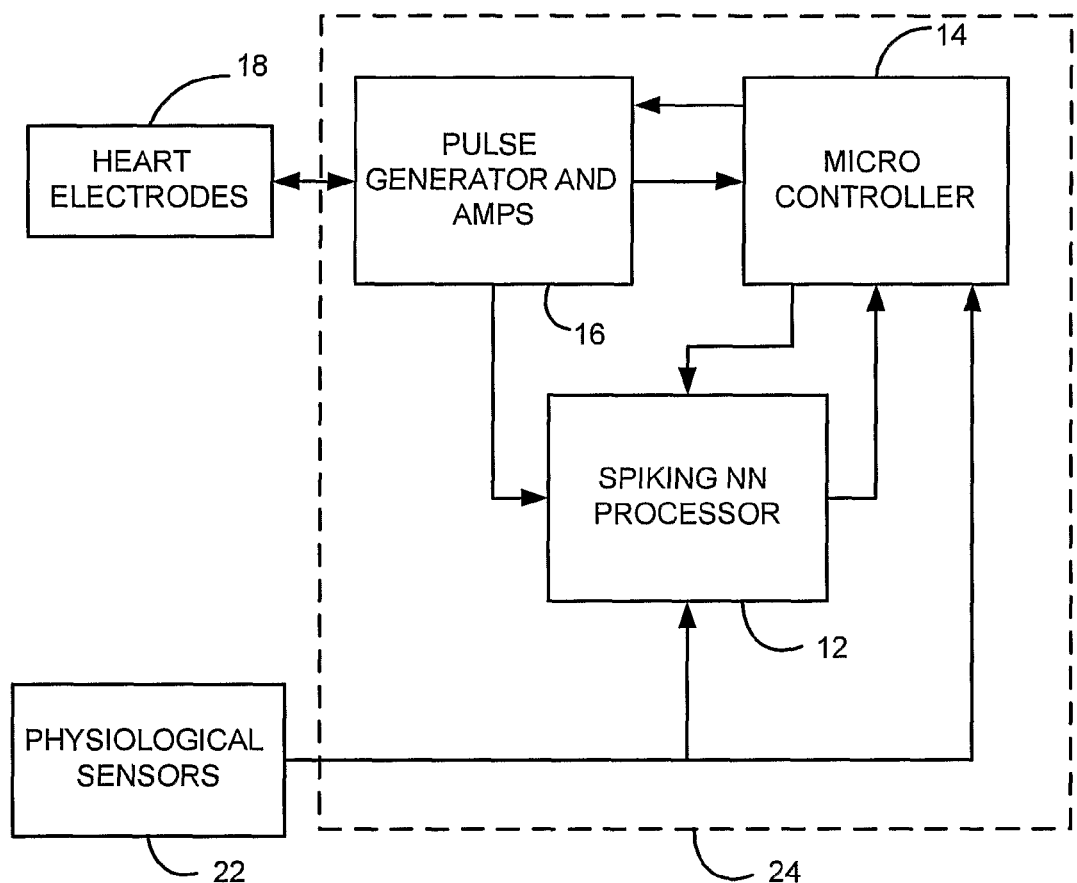
FIG. 1 is a schematic description of an adaptive CRT employing association of a ventricle-atrial (VA) interval with temporal patterns of hemodynamic sensor.

The system of the present invention employs an implanted adaptive biventricular pacemaker (referred to also as a CRT devices), or adaptive dual chamber pacemakers or ICD devices as disclosed in PCT application WO 2005007075 by the inventor of the present application, the contents of which are incorporated herein by reference. With an adaptive CRT device both AV delay and the VV interval vary dynamically in response to hemodynamic inputs from sensors in a closed loop system such that the stroke volume at a given heart rate is maximized online and continuously. This system therefore implies a feedback control. As described in FIG. 1, the system of the present invention consists of an adaptive CRT device system equipped with a neural network processor for temporal pattern detection trained to associate the next atrial event timing relative to the preceding ventricle event. Spiking neural network processor 12 is the learning module, working as a slave processor with micro-controller 14. Block 16, which represents a pulse generator and operational amplifier(s), is the analogue interface to patient heart electrodes 18. The atrial and biventricular electrodes are implanted, namely, the right atria lead, right ventricular lead and left ventricular lead. Physiologic sensors 22 implanted at the right and left ventricles, are any sensors known in the art, for example chamber impedance sensors, chamber pressure sensors and accelerometers. Box 24 designates all the modules implanted in the patient.

Figure 2:
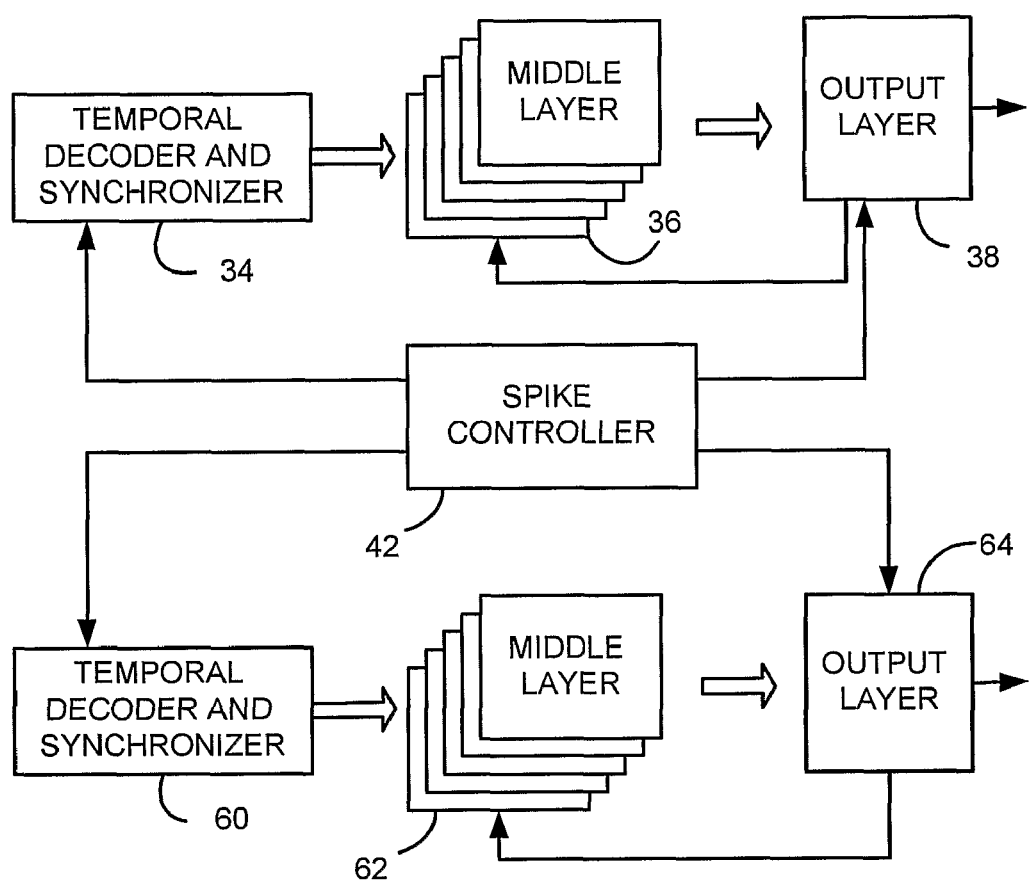
FIG. 2 is a schematic description of the neural network architecture performing biventricular pacing and VA interval association based on intracardiac electrograms (IEGMs) and hemodynamic (Impedance) sensor.

In FIG. 2 to which reference is now made, the architectural aspects of a neural network that performs both biventricular pacing and atrial event association with is temporal patterns of hemodynamic sensors are shown. Preferably, the neural network processor of the invention is a spiking neural network processor having three layers. An input layer with temporal decoder synchronizer 34, middle layer 36, and output layer 38. Spike controller 42 manages the neural network operations. The architecture of the temporal pattern detection neural network module for the atrial event timing relative to the preceding ventricle event, i.e. the VA interval, is similar to the one described above, having temporal decoder synchronizer 60, middle layer 62, and output layer 64. A detailed description of the temporal pattern detection neural network is given below. The three important outputs of the learning module, the neural network processor, are AV delay, VV interval and the associated VA interval.

The adaptive CRT neural network processor architecture and its operation is described in WO 2005/007075 the contents of which are incorporated herein by reference. The present invention provides a system and a method that in addition to bi-ventricular pacing or right ventricular pacing replace the sensed atrial event signal during atrial arrhythmia episodes with an associated VA interval internally in the timing circuits that control the ventricular and bi-ventricular pacing and are therefore capable of continuing to pace with optimal timing the ventricles during atrial fibrillation as well.

The temporal pattern detection neural network is trained using a supervised learning rule continuously supplied by the micro-controller using the hemodynamic sensor signal as an input from the right or left ventricle chambers. The neural network learns how to map the temporal patterns of the hemodynamic sensor into VA intervals as long as normal sinus rhythm is detected. Whenever atrial fibrillation occurs and is detected, the neural network associates VA interval correlated with the temporal patterns of the hemodynamic sensor that takes over the atrial sensed event as will be explained below.

Temporal Pattern Recognition with Spiking Neurons

The first stage in the temporal pattern detection neural network, is a pre-processing stage for the hemodynamic sensor temporal input signal with a temporal synchronizer. The synchronizer excites selectively an array of dynamic synapses of the middle layer. The middle layer has typically 200 dynamic synapses that are arranged in a matrix having 10 columns and 20 synapses in each column. The temporal synchronizer is triggered every cardiac cycle by the ventricle-sensed electrical event, i.e. ventricular IEGM, and following the trigger it excites selectively in a time sequence a group of dynamic synapses at each column according to the temporal values of the input hemodynamic sensor signal at the excitation times. At the output layer there are typically 10 leaky integrate-and-fires (I&F) neurons, one for each column of dynamic synapses, that accumulate the post synaptic responses excitations (PSR) of the synapses in the middle layer. All the I&F neurons are trained to fire at the same target time which is the sensed VA interval. The output layer I&F neurons are trained to fire at the target time and a fuzzy average result using a membership function for each I&F neuron is calculated as the final result of the neural network i.e. the associated VA interval. The fuzzy average calculation, to be further elaborated below, increases the prediction accuracy of the temporal pattern detection neural network (TP-DNN). The combination of fuzzy logic and neural network for control systems takes advantage of both techniques, as discussed in "Understanding Neural Networks and Fuzzy Logic: basic concepts and applications" by Stamatios V. Kartalopoulos, Wiley-IEEE Press, August 1995 incorporated herein by reference.

Temporal Pattern Recognition Learning Scheme

In 1949 Donald Hebb proposed that 'associative learning' involved a simple cellular mechanism. His hypothesis known as 'Hebb's learning rule' claimed that "coincident activity in both cells involved is critical for strengthening the connections (associations) between the pre-synaptic and post-synaptic neurons". Hebb's learning rule states that "when an axon cell A excites cell B and repeatedly or persistently takes part in firing it, some growth process or metabolic change takes place in one or both cells such that A's efficacy, as one of two cells firing B, is increased." The present invention implements Hebbian learning rules as described below The dynamic synapses of the pattern recognition network adapt their internal time delay parameter, $\tau_{ij}$, which is the time delay parameter between a pre-synaptic excitation by the temporal synchronizer to the synapse post synaptic response (PSR). The synaptic time delay parameter changes according to a supervised learning rule where the supervised target time is the sensed atrial event measured from the previous ventricle contraction. The Hebbian learning rule used with the spiking neurons network performing temporal pattern recognition of the present invention is formulated as follows:

Equation 1:

$$\tau_{ij} = \tau_{ij} + \eta * R_{ij} \qquad (1)$$

where:
i=0 . . . , 9 is the I&F neuron index and the column index.
j=0, . . . , 19 is the synapse index within a column.
$\eta$ is the learning rate coefficient.
$R_{ij}$ is a function of the relative timing of the firing of the I&F neuron, $T_i$ and the target time, $P_i$, as shown in Equation 2 below.

$$R_{ij} = \begin{cases} +1 & \text{if } T_i < P_i, \\ -1 & \text{if } T_i > P_i, \end{cases} \qquad (2)$$

In each cardiac cycle the synapses that are excited by the temporal synchronizer starts incrementing an internal counter. When the firing time of the I&F neuron, $T_i$, occurs before the internal time delay parameter, $\tau_{ij}$, expires the synapse state is stored as a Pre Hebb state. When the firing time occurs within a predefined short time interval, Δ, just after the expiration of $\tau_{ij}$ the synapse state is stored as a Hebb state. When the firing time of the I&F neuron occurs later, the synapse state is stored as a Post Hebb state. The post synaptic response (PSR) is emitted by the synapse in the Hebb state and is accumulated on the membrane potential of the post synaptic integrate and fire neuron. Note that according to Equation 2 the relative timings of the firing time $T_i$, the target time $P_i$, determines if the internal time delay parameter is incremented or decremented Associated VA interval and Hit Count Rate Membership Function A hit count rate membership function, f(Ti), is defined as the number of hits, or the hit count rate, of the I&F neuron that fires in the vicinity of the target time in a time frame of 32 cardiac cycles. The maximal value for the function is therefore 32 when the I&F neuron fires at the correct target time every cardiac cycle, and the hit count rate membership function is zero when the I&F neuron fires constantly out of the time window. For each I&F neuron the hit count rate membership function is calculated and a normalized average is calculated according to Equation 3 below $$\text{Associated VA} = \Sigma f(Ti) * Ti / \Sigma f(Ti) \quad (3)$$

Where Ti is the firing time of I&F neuron i and the summation is done over all the spiking neurons of the output layer.

Equation 3 defines the associated VA interval of the TPDNN using the hit count rate membership function. The associated VA is used later to replace the sensed VA interval during atrial fibrillation episodes.

Figure 3:
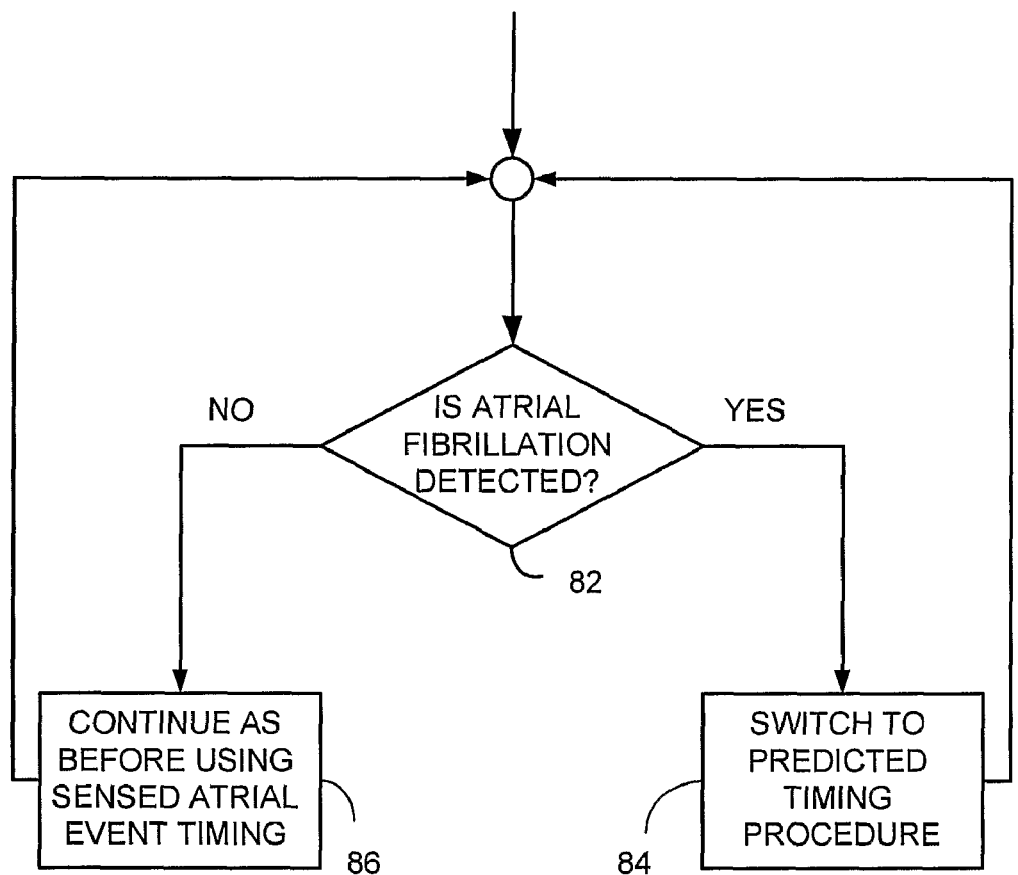
FIG. 3 is a flow diagram description of the switching between associated ventricle-atrial (VA) interval and sensed atrial event timing based pacing according to atrial fibrillation detection.

In FIG. 3 to which reference is now made, a flow diagram describes the switching decision the system makes between a sensed timing based pacing procedure and the associated timing based pacing procedure. In step 82 the atrial fibrillation detection unit verifies the presence of atrial fibrillation. If fibrillation is detected, the supervised training task is turned off, the neural network synaptic weights are frozen, and the associated VA interval is obtained in step 84 from the TPDNN as given in Eq. 3 above, is obtained beat after beat with the hemodynamic sensor input used as reference. The associated VA interval replaces the sensed atrial event for synchronizing the bi-ventricular pacing feedback task performed by the adaptive CRT device described in FIG. 2 to which reference is again made. If fibrillation is not detected, pacing continues according to the sensed atrial event during normal sinus rhythm in step 86. In this manner the CRT task continues undisturbed during an atrial fibrillation episode. The bi-ventricular pacing feedback task as explained in details in International Patent publication WO 2005/007075, for example, can continue to resynchronise the AV delay and VV timings online during a fibrillation episode. In such case, the system uses the hemodynamic sensors temporal patterns as reference, being relative to the associated VA event that replaces the normal sensed atrial event. When a normal atrial sinus rhythm is recovered, the device controller is switched back to using the natural detected atrial signal and also the VA association supervised learning task continues to learn to associate the hemodynamic sensor input temporal patterns into a VA intervals as explained above. It should be stressed that the two back and forth is switching mechanisms described above, i.e. the adaptive CRT vs. non adaptive CRT operational modes and the sensed atrial event vs. associated VA interval operational modes are independent of each other.

In the case of atrial fibrillation which is conducted to the ventricle, the hemodynamic performance of the ventricle will also be disturbed significantly and the association of the VA interval can fail. In such case the ventricular pacing relating to the associated VA interval is stopped and anti-tachycardia pacing (ATP) or a defibrillation shock might be the only effective therapy that can recover normal heart rhythm and function.

Figure 4:
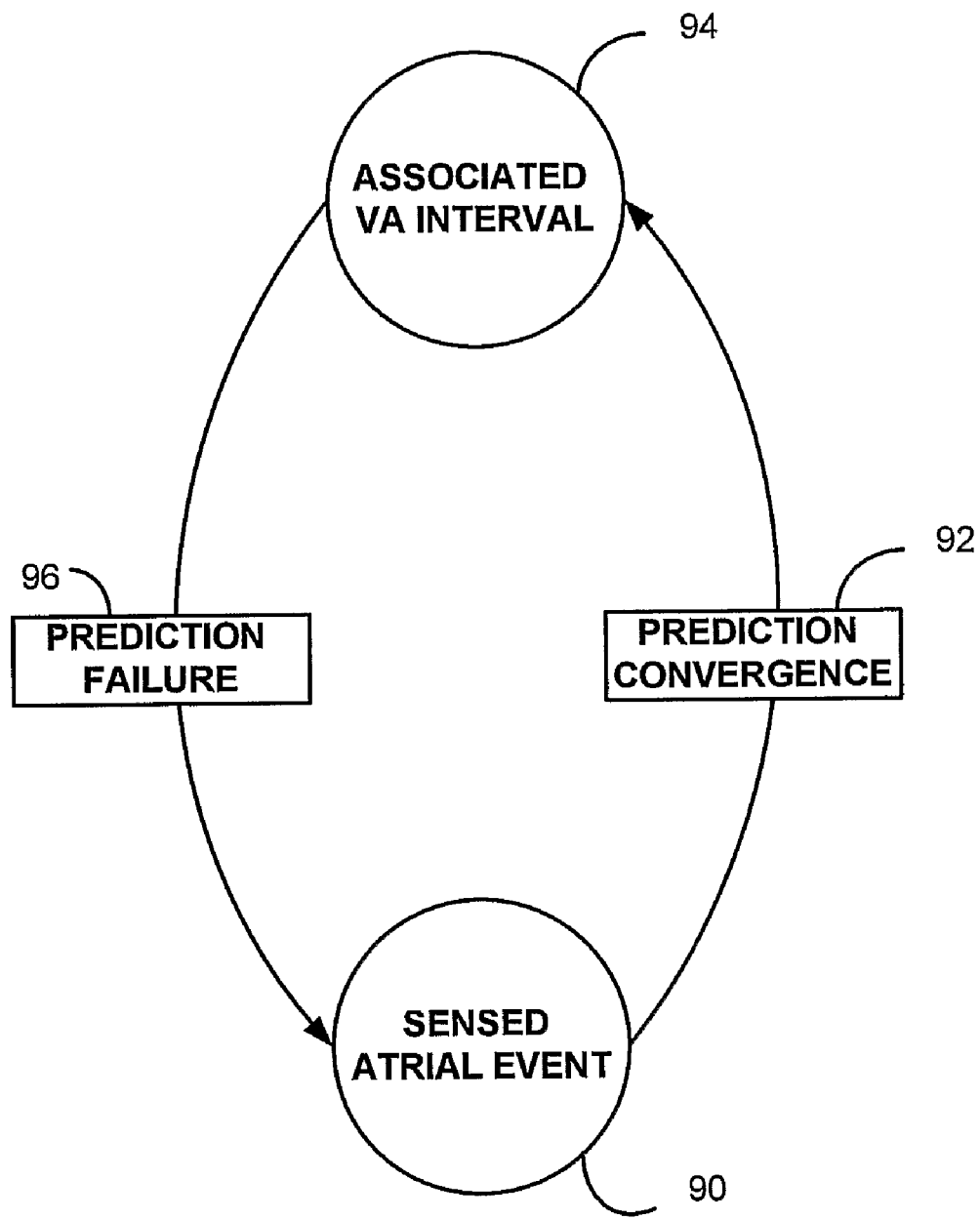
FIG. 4 is a state diagram describing switching between associated and sensed atrial timing based pacing.

In FIG. 4 to which reference is now made, a state diagram relating to another preferred embodiment of the present invention is described. In accordance with this embodiment the control system switches back and forth between two states. One state uses associated VA interval instead of the sensed atrial event, also with a normal sinus rate. The other state uses the sensed atrial event. The system initializes with sense operation mode, 90, after the convergence of the VA association task 92 it switches to operate according to the associated VA interval, and the sensed VA interval is used thereafter only for on-line supervised learning while the associated VA interval value is used for the timing cycles of the micro-controller replacing the sensed atrial event in operation mode 94. When a failure takes place, such as a large deviation of the associated VA interval from the sensed atrial event or any other pre-defined failure, the system switches back, in transition 96, to use the sensed atrial event.

There are two reasons to prefer working with the associated operation mode. First, the learned VA intervals association according to hemodynamic sensor temporal patterns reflects closely the hemodynamic cycle, i.e. the diastolic and systolic cycles and even more specifically the passive and active filling times, the iso-volumetric contraction and the ejection phase. Therefore, the associated operation mode can be a more accurate indication for cardiac cycle timing associated with implanted pacemaker systems then the local sensed atrial IEGM signal. It is assumed therefore that by using the associated VA interval according to hemodynamic sensor temporal patterns, better pacing can be achieved with better AV synchrony to produce better clinical results as compared to synchronizing based on the sensed IEGM atrial lead. Second, when the prediction error is smaller than the accumulated errors due to all noise sources in the system, such as possible lead movements and signal degradation, sampling and digitization errors, and any other noise in the implanted electronic circuits, the learned associated atrial event is closer to the underlying physiological system timings and can correct the accumulated error.

Synaptic Stability—plasticity Dilemma

What are the steady state optimal values of the synaptic weights that provide the best performance? It depends on the neural network architecture and also on environmental variables that might change with time. Hence the optimal synaptic weights are functional of time and environment states and when the environment is dynamic, such as the heart muscle, the neural network architecture must be flexible enough to adapt its synaptic weights accordingly to ensure best performance. Therefore, in accordance with the present invention the steady state value of the synaptic weight are changeable with time with the present application. In his above cited book, Stamatios V. Kartalopoulos, in page 59, discusses the notion of elasticity of the learning system. It is discussed how a learning system can be designed to remain plastic or adaptable enough to learn new things whenever they appear and yet remain stable enough to retain previously learned knowledge.

With the neural network temporal pattern recognition architecture presented here each synapse change its learning rate parameter, η, according to its local activation state and a value of the membership function calculated for each I&F neuron, i.e. the hit count rate. When the dynamic synapse is highly activated in Hebb state and the hit count rate is high, the learning rate, η, is decreased and hence synapse gains selective stability. The mechanism for adjusting selectively the learning rate parameter brings stability and reduces the occurrence of losing previously learned patterns by new input patterns. A neural network system employing a smaller learning rate parameter becomes a slow learner but still maintains a reduced plasticity. New patterns that excite other synapses in the middle layer will be processed with higher plasticity according to the selective stabilization mechanism described here. The selective stabilization process is improved further by adding a global small leakage component to all synapse excitation that cause a loss of activation with a constant slow rate. This mechanism affects synapses that were previously highly activated but later became inactive for a long period of time, to lose slowly their activation level and thus to increase their plasticity through acquiring a larger learning rate coefficient.

In accordance with the present invention, the spiking neural network architecture strategy is to change for each synapse the learning rate coefficient locally and selectively. Synapses that were active and cause hits at the target time and hence a saturation of the hit count rate membership function gain stability. The neural network architecture described above demonstrates both plasticity and stability, and is more stable with regards to noise and erroneous temporal patterns, yet it is still a fast learner of new temporal patterns due to the selectivity of the learned learning rate coefficients.

ADVANTAGES OF IMPLEMENTING THE INVENTION

Applying the method of the present invention, the ventricular pacing is synchronized with the cardiac cycle timings even during atrial fibrillation and hence can unload hemodynamic stress and may further suppress the arrhythmia, according to argumentation of Taggart and Sutton quoted above. It is expected to be clinically beneficial for both congestive heart failure (CHF) patients treated with CRT devices and for patients treated with dual chamber pacemakers and ICD's.

The invention claimed is:

1. A cardiac resynchronization system for delivering biventricular stimulation to the heart correlated with hemodynamic performance of the heart, comprising:
    a. at least one hemodynamic sensor for monitoring said hemodynamic performance of the heart;
    b. an atrial electrode and at least two ventricular electrodes, adapted to sense ventricular and atrial signals;
    c. a learning module comprising a spiking neural network processor adapted to learn to associate the ventricular-atrial intervals sensed by said electrodes with the hemodynamic performance sensed by said at least one hemodynamic sensor, and calculate ventricular-atrial intervals and replace said ventricular-atrial intervals calculated from the sensed ventricular and atrial signals with the learned associated ventricular-atrial intervals and cause delivery according to the learned associated ventricular-atrial intervals a biventricular stimulation to the heart during atrial fibrillation episodes, wherein said spiking neural network processor further comprises:
    I. an input layer temporal synchronizer performing a preprocessing stage of said hemodynamic performance of the heart sensed by said at least one hemodynamic sensor;
    II. a middle layer comprising of an array of dynamic synapses, wherein said dynamic synapses are grouped in columns, and
    III. an output layer comprising at least one integrate and fire neuron for each said dynamic synapse column of the middle layer, said at least one integrate and fire neuron being adapted to perform said learning to associate ventricular-atrial intervals with said hemodynamic performance of the heart;
    d. a micro controller for controlling said learning module, and
    e. at least one pulse generator and operational amplifier controlled by said micro controller for stimulating the heart with said biventricular stimulation.

2. A system according to claim 1 wherein the synapses of the middle layer of said spiking neural network processor have a learning rate parameter, and said synapses are self-trained applying a Hebbian learning rule and said synapses locally and selectively change the learning rate parameter in each synapse module according to a value of a hit count rate membership function calculated by a post synaptic integrate and fire neuron according to an activation state of a synapse such that a synapse decreases its learning rate after said synapse was active and caused a saturation of said hit count rate membership function of an output layer integrate and fire neuron.

3. A system according to claim 1, wherein each said synapse is adapted to adjust a local and selective learning rate parameter separately in order to improve stability and preserve plasticity of said spiking neural network processor.

4. A system according to claim 1, said system learns to associate said ventricular-atrial interval based on said hemodynamic performance of the heart wherein the associated ventricular-atrial interval replaces a sensed atrial event signal during atrial fibrillation episodes, wherein said system is implementable as an adaptive dual chamber pacemaker and/or cardioverter defibrillator, delivering said biventricular stimulation to the heart with dynamic atrio-ventricular delay wherein said stimulation is adapted continuously to the hemodynamic performance of the heart.

5. A system according to claim 1, wherein said spiking neuron neural network is adapted to be implementable in a processor operating with low clock frequency at the range 1-10 KHz and with synaptic weight adaptation deriving reference from an input of said hemodynamic sensor and implementing a Hebbian learning rule.

6. A system as in claim 1, adapted to determine the validity of the ventricular-atrial interval associated with the spiking neural network processor, and to determine whether a ventricular-atrial interval association is poor or whether any system failure has occurred, wherein the associated ventricular-atrial interval replaces a sensed atrial event signal as long as the ventricular-atrial interval associated with said spiking neural network is valid and where said cardiac resynchronization system is adapted to switch back to working with said sensed event when the ventricular-atrial interval association is poor or any system failure occurs, said system being adapted to: (a) sense an atrial operation mode and an associated ventricular-atrial interval operation mode, (b) perform a temporal pattern recognition of the spiking neural network and (c) switch back and forth between said sensed atrial operation mode and the associated ventricular-atrial interval operation mode based upon said temporal pattern recognition of the spiking neural network; whereby said system is implementable as an adaptive cardiac resynchronization system and/or dual chamber pacer and/or intracardiac cardioverter defibrillator.

7. A system as in claim 1 wherein said ventricular-atrial interval sensed by said electrodes is adapted so that it can be sensed online.

* * * * *